United States Patent
Karehill et al.

(10) Patent No.: US 6,605,303 B1
(45) Date of Patent: Aug. 12, 2003

(54) ORAL PHARMACEUTICAL EXTENDED RELEASE DOSAGE FORM

(75) Inventors: Per-Gunnar Karehill, Mölndal (SE); Per Johan Lundberg, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/555,744

(22) PCT Filed: Dec. 17, 1998

(86) PCT No.: PCT/SE98/02368

§ 371 (c)(1), (2), (4) Date: Jan. 15, 1999

(87) PCT Pub. No.: WO99/32091

PCT Pub. Date: Jul. 1, 1999

(30) Foreign Application Priority Data

Dec. 22, 1997 (SE) ................................................ 9704869

(51) Int. Cl.[7] ............................ A61K 9/14; A61K 9/26; A61K 9/20; A61K 9/22; A61K 9/16

(52) U.S. Cl. ........................ 424/484; 424/470; 424/464; 424/468; 424/469; 424/451; 424/497; 424/480; 424/494; 424/474

(58) Field of Search .................................. 424/484, 470, 424/464, 468, 469, 451, 497, 480, 474, 494

(56) References Cited

U.S. PATENT DOCUMENTS

| 5,945,124 | A | * | 8/1999 | Sachs et al. | .................. 424/472 |
| 6,068,856 | A | | 5/2000 | Sachs et al. | .................. 424/474 |
| 6,132,768 | A | | 10/2000 | Sachs et al. | .................. 424/458 |
| 6,136,344 | A | * | 10/2000 | Depui et al. | .................. 424/470 |
| 6,274,173 | B1 | | 8/2001 | Sachs et al. | .................. 424/480 |

FOREIGN PATENT DOCUMENTS

| EP | 0 514 008 | * | 11/1992 |
| EP | 0514008 | | 11/1992 |
| EP | 0 526 862 | * | 2/1993 |
| EP | 0526862 | | 2/1993 |
| WO | 9702020 | | 1/1997 |
| WO | 9747285 | | 12/1997 |

* cited by examiner

*Primary Examiner*—Thurman K. Page
*Assistant Examiner*—Blessing Fubara
(74) *Attorney, Agent, or Firm*—White & Case LLP

(57) ABSTRACT

An enteric coated pharmaceutical extended release dosage form of a $H^+$, $K^+$-ATPase inhibitor giving an extended plasma concentration profile of a $H^+$, $K^+$-ATPase inhibitor. The extended plasma profile is obtained by a pharmaceutical composition which comprises a core material of a hydrophilic or hydrophobic matrix, and the $H^+$, $K^+$-ATPase inhibitor and optionally pharmaceutically acceptable excipients. The dosage form may be administered once daily.

31 Claims, No Drawings

ORAL PHARMACEUTICAL EXTENDED RELEASE DOSAGE FORM

FIELD OF THE INVENTION

The present invention is related to new pharmaceutical dosage forms which comprise a proton pump inhibitor, i.e. a $H^+,K^+$-ATPase inhibitor. The new dosage forms are enteric coated formulations which provide an extended and continuous release of the $H^+,K^+$-ATPase inhibitor in the small and/or large intestines resulting in an extended blood plasma profile. The formulations comprise a hydrophilic or hydrophobic matrix resulting in an extended release of the $H^+,K^+$-ATPase inhibitor preferably for a minimum of 2 and a maximum of 12 hours. Furthermore, the present invention refers to the manufacture of such extended release pharmaceutical formulations, and their use in medicine.

BACKGROUND OF THE INVENTION AND PRIOR ART

Acid labile $H^+,K^+$-ATPase inhibitors also named as gastric proton pump inhibitors are for instance compounds known under the generic names omeprazole, lansoprazole, pantoprazole, rabeprazole and leminoprazole. Some of these compounds are disclosed in EP-A1-0005129, EP-A1-124495, WO 94/27988, EP-A1-174726, EP-A1-166287 and GB 2163747.

These pharmaceutical substances are useful for inhibiting gastric acid secretion in mammals including man by controlling gastric acid secretion at the final step of the acid secretory pathway and thus reduce basal and stimulated gastric acid secretion irrespective of stimulus. In a more general sense, they may be used for prevention and treatment of gastric-acid related diseases in mammals and man, including e.g. reflux oesophagitis, gastritis, duodenitis, gastric ulcer, duodenal ulcer and Zollinger-Ellison syndrome. Furthermore, they may be used for treatment of other gastrointestinal disorders where gastric acid inhibitory effect is desirable e.g. in patients on NSAID therapy, in patients with Non Ulcer Dyspepsia, and in patients with symptomatic gastro-oesophageal reflux disease (GORD). They may also be used in patients in intensive care situations, in patients with acute upper gastrointestinal bleeding, pre-and postoperatively to prevent aspiration of gastric acid and to prevent and treat stress ulceration. Further, they may be useful in the treatment of psoriasis as well as in the treatment of Helicobacter infections and diseases related to these.

Therapeutic control of gastric acid secretion is fundamental in all theses diseases, but the degree and duration of acid inhibition required for optimal clinical effect is not fully understood.

It has been proposed by the Applicant in WO97/48380 (published Dec. 24, 1997, i.e. after the priority date of the present application) that an administration regimen that gives blood plasma levels extending from 2 to 2 hours (by any of several means) will result in a larger fraction of the proton pumps being inhibited. Thus, an extended blood plasma level should result in more effective inhibition of acid secretion resulting in improved efficacy in GORD, more rapid healing of gastric ulcer and improved eradication of *H. Pylori*. The present invention provides pharmaceutical dosage forms which achieve such extended plasma levels by an extended release of the drug.

A pharmaceutical dosage form comprising omeprazole or any other proton pump inhibitor is best protected from contact with acidic gastric juice by an enteric coating layer. In U.S. Pat. No. 4,786,505 and U.S. Pat. No. 4,853,230 such enteric coated preparations are described. These preparations have a core comprising an alkaline salt of the drug or a core comprising the drug together with an alkaline reacting compound. The core is coated with a water soluble or in water rapidly disintegrating separating layer and then with an enteric coating layer. WO 96/01623 and WO 96/01624 describe tableted dosage forms of omeprazole and other proton pump inhibitors, wherein enteric coating layered pellets are compressed into a multiple unit tableted dosage form. It is essential in these tableted formulations that the enteric coating layer can withstand the compression forces. None of these by the Applicant previously described formulations gave an extended release of the drug which resulted in an extended blood plasma profile.

WO 97/02020 describes a dosage form for pantoprazol together with an antibiotic substance, which dosage form has a release-slowing membrane positioned as a intermediate layer. Said membrane comprises a water-insoluble film-forming agent as an important feature of the dosage forms. WO 97/02021 describes the same type of dosage form for a reversible proton pump inhibitor in combination with an antibiotic substance.

A facilitated way to produce extended release dosage forms compared to applying a semipermeable membrane, is to make a dosage form comprising a matrix unit. Some advantages of such matrices are for instance easier processing methods mainly by the use of common granulating and tableting equipment, and sometimes also with regard to solvents handling, energy and production time gain etc.

The use of hydrophilic matrix tablets as a principle for extended drug release was first A described in the early 60's, see for instance U.S. Pat. No. 3,065,143. Also the hydrophobic matrix tablet principle for extended release originates from the 60's, for instance quinidine dureles were on the market in 1963.

Extended release dosage forms comprising different drugs in a matrix have been described in prior art. However, none of these matrix dosage forms as such is suitable for a $H^+,K^+$-ATPase inhibitor.

Some extended release hydrophilic matrix dosage forms are described in the literature for instance: In Journal of Pharmaceutical Sciences vol. 84, No. 3, March 1995, in which Kim describes dosage forms comprising theophylline or diltiazem hydrochloride. U.S. Pat. No. 5,273,758 describes dosage forms comprising for instance clemastine fumarate. EP 0249587 discusses felodipine formulations. Dosage forms comprising a benzodiazepine derivative are described by Franz et al in Journal of Controlled Release 1987, 5, 159–72.

Dosage forms comprising an extended release hydrophobic matrix have been described for instance by Romero et al in International Journal of Pharmacy 1991, 73, 239–48.

Extended release tablets with an additional coating layer have also been described, for instance by Sangalli et al in International Journal of Pharmaceutics, 91(1993), 151–6. The drugs exemplified are metoprolol tartrate and benfluorex. The described dosage form has an impermeable coating which is perforated to achieve a hole in the middle of the tablet, exposing a starting surface area for the dissolution of the inner core, i.e. dissolution of the active drug.

A rather complicated dosage form was described in U.S. Pat. No. 5,178,867. The dosage forms had a core comprising a drug which core was coated with a semipermeable wall (maintaining its physical integrity during the life-time of the dosage form) having at least one hole drilled through it as an exit port for the dissolved drug. It is also mentioned that an enteric coating layer may be applied for restricting drug delivery in the stomach and for providing drug release in the small intestine. This dosage form is much more complicated to manufacture than a matrix unit. There is no detailed description of a prepared dosage form comprising a proton pump inhibitor compound and testing of such a dosage form to assure that no acidic gastric fluid is penetrating the semipermeable membrane, and that the active substance is delivered intact to the site of absorption.

None of these dosage forms provides an easy-to-produce matrix dosage form which protect an acidic susceptible substance such as a proton pump inhibitor against degradation which occurs in contact with an acidic milieu such as the one found in the stomach.

SUMMARY OF THE INVENTION

Thus, the present invention relates to an enteric coated formulation with extended release properties comprising a hydrophilic or hydrophobic matrix, in which a $H^+,K^+$-ATPase inhibitor or one single enantiomer thereof, or an alkaline salt of the $H^+,K^+$-ATPase inhibitor or one of its single enantiomers is incorporated.

The present invention provides a solution to the problem of making in a simplified manner such extended release dosage forms comprising an acidic susceptible $H^+K^+$-ATPase inhibitor, such as omeprazole or another proton pump inhibitor. A specific problem is that the pharmaceutical dosage forms according to the present invention must fulfill certain requirements with respect to gastric acid resistance for enteric coated articles specified in the US Pharmacopeia (Edition 23), such as the dosage form has to be protected by an enteric coating to ensure safe delivery of the intact drug to the proper site in the gastrointestinal channel where it may be absorbed.

According to the present invention the extended plasma profile is provided by once daily administration of an enteric coated dosage form which releases the proton pump inhibitor during an extended time period, preferable during a minimum period of 2 hours and a maximum period of 12 hours. Thus, the complete dose shall have been delivered within 2 hours or at a maximum within 12 hours. The therapeutic effect of omeprazole and similar substances may be improved by providing an extended plasma profile and by providing such a dosage form for a once daily administration.

The present extended release formulations show an improved patient compliance over an administration regimen comprising consecutive administration of two or more unit doses during one day.

DETAILED DESCRIPTION OF THE INVENTION

The dosage forms giving extended release according to the present invention, are units in the form of enteric coated tablets. Alternatively, the units are enteric coated pellets, which pellets are filled into a capsule or together with tablet excipients compressed into a multiple unit tableted dosage form.

The individual units, i.e. tablets or pellets, may be constructed as a a core material, optionally layered on a seed/sphere, the core material comprising a hydrophilic or hydrophobic matrix containing the active drug and optionally pharmaceutically acceptable excipients, and an optional surrounding separating layer, and finally an enteric coating layer.

Core Material

The core material for the units, i.e. the tablets or the individual pellets can be constituted according to different principles. The core material may be homogenous or heterogeneous.

I) Homogenous Core Material.

If the core material is homogenous, it has a homogenous distribution of active substance throughout the core material.

The active substance is mixed with substances forming a hydrophilic or hydrophobic matrix and optionally pharmaceutically acceptable excipients. The core material should be free from acidic substance. Thus, the hydrophilic hydrophobic matrix in combination with other material in the core must not create an acidic reaction in the core material, which would be deleterious to the acid susceptable proton pump inhibitor compound. The micro environment around the proton pump inhibitor compound should preferably have a pH of not less than pH=7, more preferably not less than pH=8, when water is absorbed to the particles of the mixture or when water is added in small amount to the mixture.

The active substance may be mixed with further components to obtain preferred handling and processing properties and a suitable concentration of the active substance in the final mixture. Such components can be binders, surfactants, lubricants, glidants, fillers, alkaline additives or other pharmaceutically acceptable ingredients, alone or in mixtures.

Said core material may be produced either by direct compression of the mixed ingredients, or by granulation of the ingredients followed by compression of the dried granulated material.

In direct compression, the ingredients are mixed and compressed by using ordinary tableting equipment.

For the granulation there are numerous alternatives of granulating procedures mentioned in the literature, dry methods like roller compaction (Chilsonator) and wet methods Utilizing granulating solutions with and without the addition of binders. A variant of the wet methods is to make a spray-granulation in a fluid bed.

For the wet granulating methods either organic solvents, aqueous solutions or pure water may be utilized to prepare the granulating solutions. Due to environmental considerations pure water is preferred. However, for some of the materials used as hydrophilic matrix components, the technical properties of the produced granules might be better when using organic solvents such as alcohols. This is especially noticeable for hydroxypropyl methylcelluloses.

For granulation of the hydrophobic matrix components it is also preferred to use alcoholic solvents in wet granulation methods. As binders in these solution, one or more of the polymers listed below, as matrix forming polymers may be chosen.

As a general principle the active ingredients together with matrix forming polymers and optionally pharmaceutically acceptable excipients are mixed and granulated. Dried granules are optionally mixed with pharmaceutically acceptable excipients, and then compressed to tablets utilizing common equipment.

The size of the formulated core materials is approximately between 2 and 14 mm, preferably between 3 and 9 mm for a tablet preparation, and between 0.1 and 4 mm, preferably between 0.1 and 2 mm for a pellet preparation.

II) Heterogenous Core Material

Alternatively, the core material may be heterogeneous with an inner zone, for instance a seed or sphere, not containing the active substance. This seed or sphere is surrounded by a layer of a hydrophilic or hydrophobic matrix containing the active substance, and optionally pharmaceutically acceptable excipients are incorporated in the matrix.

The seed or sphere may be soluble or insoluble. Optionally, the seed or sphere (inner zone) may be coated with an inert layer to prepare a smooth surface before the layer containing active substance and hydrophilic or hydrophobic eroding substance(s) is applied onto the seed/sphere.

Insoluble seeds/spheres may comprise different oxides, celluloses, organic polymers and other materials, alone or in mixtures. Water soluble seeds/spheres may comprise different inorganic salts, sugars and other materials, alone or in mixtures. The size of the seeds may vary between approximately 0.1 and 2 mm. The seeds layered with the matrix containing the active substance are produced either by powder or solution/suspension layering using for instance granulating or spray coating/layering equipment.

Pharmaceutically Acceptable Additives.

Binders for a hydrophilic matrix can be chosen among the hydrophilic eroding matrices mentioned below, and in addition from sugars, polyvinyl pyrrolidine, starches and gelatine.

Binders for a hydrophobic matrix can be chosen among the hydrophobic eroding matrices mentioned below.

Additives listed among the following components are suitable both for a hydrophilic as well as a hydrophobic matrix.

Suitable alkaline additives can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3 \cdot 6MgO \cdot CO_2 \cdot 12H_2O$, $(Mg_6Al_2(OH)_{16}CO_3 \cdot 4H_2O)$, $MgO \cdot Al_2O_3 \cdot 2SiO_2 \cdot nH_2O$ or similar compounds; organic pH-buffering substances such as trihydroxymethylaminomethane, basic amino acids such as arginine, and their salts or other similar pharmaceutically acceptable pH-buffering substances.

Suitable surfactants are found in the groups of pharmaceutically acceptable non-ionic surfactants, such as polysorbate 80, or ionic surfactants such as for instance sodium lauryl sulfate.

Lubricants are for instance magnesium stearate, sodium stearyl fumarate (Pruv™), and cetyl palmitate.

Fillers are for instance sodium aluminium silicate, lactose, calcium phosphate, and others.

Glidants are for instance talc and aerosil.

Antioxidants may be added when appropriate.

Active Substance.

Compounds of interest for the novel extended release dosage forms according to the present invention are compounds of the general formula I, an alkaline salt thereof, one of the single enantiomers thereof or an alkaline salt of one of the enantiomers

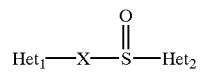

wherein $Het_1$ is

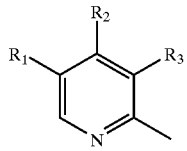 or 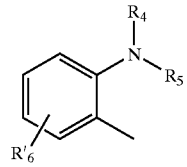

$Het_2$ is

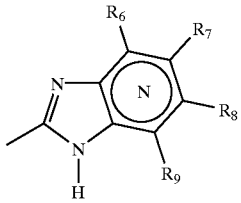 or 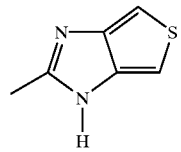

X=

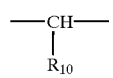 or 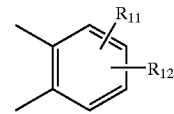

wherein

N in the benzimidazole moiety means that one of the ring carbon atoms substituted by $R_6-R_9$ optionally may be exchanged for a nitrogen atom without any substituents;

$R_1$, $R_2$ and $R_3$ are the same or different and selected from hydrogen, alky, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and arylalkyl;

$R_6'$ is hydrogen, halogen, trifluoromethyl, alkyl or alkoxy;

$R_6-R_9$ are the same or different and selected from hydrogen, alkyl, alkoxy, halogen, halo alkoxy, alkylcarbonyl, alkoxycarbonyl, oxazolinyl, trifluoroalkyl, or adjacent groups $R_6-R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl.

Examples of specifically interesting compounds according to formula I are

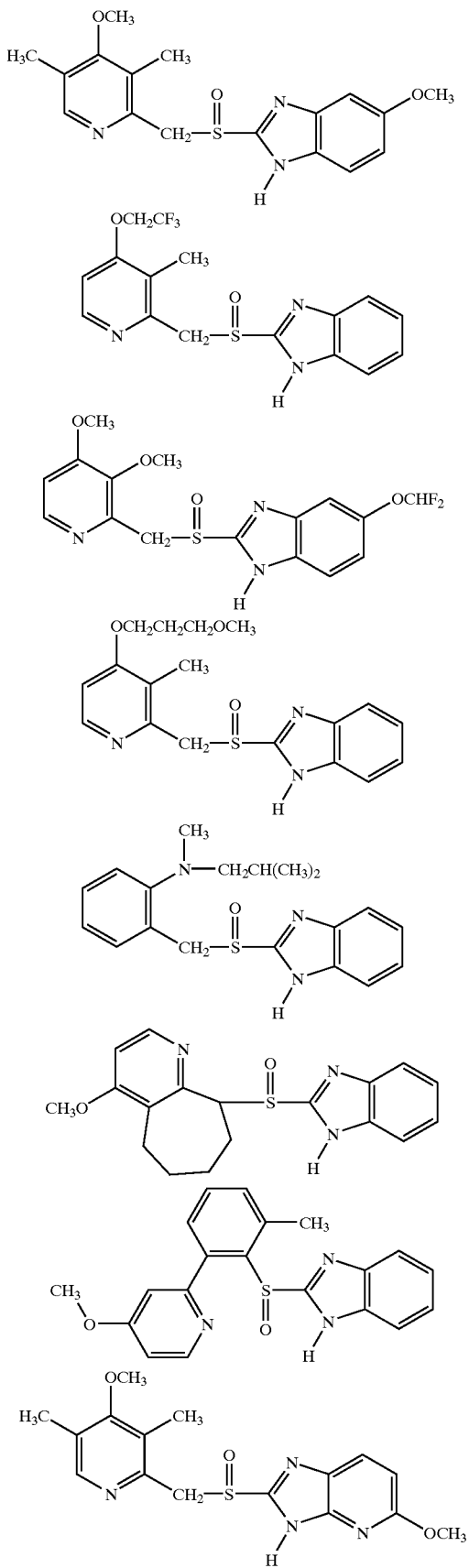

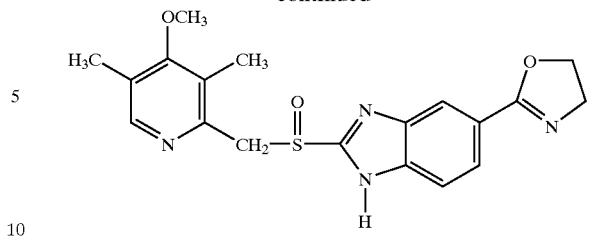

The compound suitable to be used in the extended release formulations according to the present invention may be used in neutral form or in the form of an alkaline salt, such as for instance the $Mg^{2+}$, $Ca^{2+}$, $Na^+$ or $K^+$ salts, preferably the $Mg^{2+}$ salts. The compounds may also be used in the form of one of its single enantiomers or an alkaline salt of the single enantiomer.

Preferred compounds for the oral pharmaceutical preparations according to the present invention are omeprazole, a magnesium salt of omeprazole or a magnesium salt of the (−)-enantiomer of omeprazole. Omeprazole and related substances as well as their preparations are described in EP 5129, EP 124 495, WO 95/01977, WO 94/27988 hereby incorporated in a whole by reference.

The above compounds are susceptible to degradation/transformation in acidic and neutral media. Generally, the degradation is catalyzed by acidic reacting compounds and the active compounds are stabilized with alkaline reacting compounds. There are different enteric coating layered preparations comprising omeprazole as well as other proton pump inhibitors described in the prior art, see for instance U.S. Pat. No. 4,853,230, WO 95/01783 and WO 96/01623. Especially, the latter describes alternative manufacturing methods for the preparation of enteric coating layered pellets comprising omeprazole and similar compounds. These patents are hereby incorporated in whole by reference.

Hydrophilic Matrix.

The active substance, i.e. the drug, is embedded in a hydrophilic polymer optionally together with pharmaceutically acceptable excipients. Suitable hydrophilic polymers are for instance hydroxypropyl methylcellulose, hydroxypropyl cellulose, ethylhydroxy ethylcellulose, hydroxyethyl cellulose, carboxymethyl cellulose, sodium carboxymethyl cellulose, methyl cellulose, polyethylene oxides, polyvinyl alcohols, tragacanth, and xanthan. These polymers can be used alone or in mixtures with each other.

The amount of hydrophilic polymer in the matrix is preferably 15–80% (calculated on the unit weight), and the hydrophilic polymer(s) chosen among the above mentioned.

Especially preferred polymers in the hydrophilic matrix unit are hydroxypropyl methylcellulose or polyethylene oxides.

Excipients preferred in the matrix are fillers which result in good technical tableting properties, i.e. sodium aluminium silicate, mannitol or calcium phosphate (Emcompress™). A preferred matrix comprises 15–80% w/w (calculated on the unit weight) of a hydrophilic polymer chosen as above, and 10–60% w/w (calculated on the unit weight) of sodium aluminium silicate or calcium phosphate (Emcompress™).

Hydrophobic Matrix.

The active substance, i.e. the drug, is embedded in a hydrophobic matrix optionally together with pharmaceutically acceptable excipients. The hydrophobic matrix comprises a hydrophobizing agent and/or a hydrophobic polymer. Suitable material for the hydrophobic matrix are for instance a hydrophobizing agents such as cetanol, cetostearyl alcohol, cetyl palmitate, waxes lice carnauba wax, paraffin, magnesium stearate, sodium stearyl fumarate, and medium- or long-chain glycerol esters alone or in any mixtures. Hydrophobic polymers are exemplified by for instance polyvinyl chloride, ethyl cellulose, polyvinyl acetate and acrylic acid copolymers, such as Eudragith™ RS and RL. The polymers can be used alone or as mixtures.

As binders for the hydrophobic matrix, either hydrophilic or hydrophobic may be used polymers.

It is important that the matrix comprises at least one component that is soluble in media such as the intestinal fluids. This component dissolves and leaves a porous network open for passage of dissolving fluids and dissolved drug. This soluble component may be the active drug itself, or a soluble component such as a sugar. Preferably the soluble component is present in an amount of not less than 2% w/w (calculated on the unit weight) and up to 60%.

It is preferred that the matrix comprises not less than 10% w/w (calculated on the unit weight) and up to 80% of a hydrophobizing agent or a hydrophobic polymer, both described above, or any combinations thereof.

Another preferred matrix comprises as an additive a slightly soluble or less soluble component. As such any of the following components may be added: sodium aluminium silicate, calciumphosphate, aerosil, titanium dioxide, magnesium carbonates, or other neutral or alkaline compounds that are slightly soluble or less soluble, herein with regard to solubility in water. Slightly soluble is defined in compliance with the European Pharmacopiea (Edition 3) under the heading "General notices". Such a matrix comprises 10–80% w/w (calculated on the unit weight) of a hydrophobizing agent or a hydrophobic polymer or any combinations thereof, together with 10%–60% of a slightly soluble or less. soluble component. As such an especially preferred component is sodium aluminium silicate.

The final dissolution profile may sometimes be adjusted by thermal treatment of the hydrophobic matrix unit for a short period, to achieve temperatures at or above the softening temperature of the hydrophobizing agents. Such a treatment is most suitably performed after the enteric coating has been completed.

Enteric Coating Layer(s) and Separating Layer(s).

Before applying an enteric coating layer onto the core material, the pellet or tablet may optionally be covered with one or more separating layers comprising pharmaceutical excipients optionally including alkaline compounds such as for instance pH-buffering compounds. This separating layer separates the active substance in the pellets or tablets from the outer enteric coating layer.

The separating layer can be applied by coating or layering procedures in suitable equipment such as a coating pan, coating granulator, centrifugal granulator in a fluidized bed apparatus (including Wuster type) using water and/or organic solvents for the coating process. As an alternative the layer(s) can be applied by using powder coating or press-coating techniques.

Suitable materials for the separating layer are pharmaceutically acceptable compounds such as, for instance, sugar, polyethylene glycol, polyvinyl pyriolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static to agents, such as for instance magnesium stearate, titanium dioxide, talc, pH-buffering substances and other additives may also be included into the separating layer.

When the optional separating layer is applied to the pellets or tablets it may constitute a variable thickness. The maximum thickness of the optional separating layer is normally only limited by processing conditions. The separating layer may serve as a diffusion barrier and may act as a pH-buffering zone. The optionally separating layer may improve the chemical stability of the active substance and/or the physical properties of the dosage form.

Finally the units, i.e. the tablets or pellets, are covered by one or more enteric coating layers by using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethyl ethylcellulose, shellac or other suitable enteric coating layer polymer(s).

Additives such as dispersants, colorants, pigments, additional polymers e.g. poly(ethylacrylate, methylmethacrylate), anti-tacking and anti-foaming agents may also be included into the enteric coating layer. Other compounds may be added to increase film thickness and to decrease diffusion of acidic gastric juices into the acid susceptible material. The enteric coating layer(s) constitutes a thickness of approximately at least 10 $\mu$m, preferably more than 20 $\mu$m. The maximum thickness of the applied enteric coating layer(s) is normally only limited by processing conditions.

The enteric coating layers may also contain pharmaceutically acceptable plasticizers to obtain desired mechanical properties. Such plasticizers are for instance, but not restricted to, triacetin, citric acid esters, phthalic acid esters, dibutyl sebacate, cetyl alcohol, polyethylene glycols, glucerol monoesters, polysorbates or other plasticizers and mixtures thereof. The amount of plasticizer is preferably optimized for each formula, in relation to the selected polymer (s), selected plasticizer(s) and the applied amount of said polymer(s).

Final Dosage Form

The enteric coated tablet, or pellet optionally mixed with tablet excipients are filled into a capsule, or compressed into a multiple unit tableted dosage form. Prepared enteric coated tablets are optionally covered with fit forming agent(s) to obtain a smooth surface of the tablet and further enhance the stability of the tablet during packaging and transport. Such a tablet coating layer may further comprise additives like anti-tacking agents, colorants and pigments or other additives to obtain a tablet of good appearance.

The dosage forms according to the invention are suitable for oral administration. The dose will depend on the nature and severity of the disease to be treated. The dose may also vary according to the age, body weight, and response of the individual patient. Children and patients with liver diseases as well as patients under long term treatment will generally benefit from doses that are somewhat lower than the average. In the treatment of other conditions higher doses than average will be used. The dosage form may also be used in combinations with other dosage forms comprising for instance NSAID(s), motility agents, antibacterial substances, and/or antacids.

A unit dosage of the proton pump inhibitor is administered at least once a day. The oral pharmaceutical formulation will maintain an extended release of the pharmaceutical substance of a minimum of 2 and a maximum of 12 hours, preferably is maintained for a minimum of 4 and a maximum of 8 hours. Such an extended release preparation may comprise up to 500 mg of the substance, preferably the doses comprise about 5–100 mg of the substance, and more preferably 10–80 mg.

EXAMPLES

The invention is described more in detail by the following non-limiting examples.

Example 1

Extended release matrix tablets comprising Omeprazole -Mg (approx. 20 mg).

Granules for tablet cores were made according to the following composition (parts by weight);

| | |
|---|---|
| Omeprazole-Mg | 45 |
| Polyethylene oxide (m wt approx. 4000 000), Polyox ® WSR 301 | 195 |
| ethanol 95% (w/v) | 97 |

The powders were mixed in a mixer after which the ethanol was added in an even stream. The mass was dried in a drying oven at 50° C.

After milling in an oscillating mill through a 1.0 mm screen the obtained granules were mixed with tablet lubricant, according to the following composition (parts by weight);

| | |
|---|---|
| Granules for tablet core | 235 |
| Sodium stearyl fumarate (Pruv ®) | 1 |

The mixing was performed in a Kenwood mixer, and the mixture was compressed to tablets (6 mm in diameter) having an average weight of 123 mg, on a single punch tableting machine (Diaf).

The dissolution rate was tested by analyzing individual tablets using USP dissolution apparatus No. 2 (paddle) equipped with a stationary basket and operated at 100 rpm and 37° C. The dissolution medium was phosphate buffer pH 6.8.

The release rate obtained (n=2) is shown in table below;

| Time (Hours) | Released (% of dose) |
|---|---|
| 0.5 | 4–4 |
| 1 | 7–8 |
| 3 | 20–21 |
| 5 | 31–33 |
| 10 | 59–67 |
| 15 | 84–86 |
| 20 | 95–96 |

The prepared tablets can be further processed according to Example 3 or 4, i.e. apply an enteric coating on the tablet.

Example 2

Extended release matrix tablets comprising S-omeprazole Mg-salt (approx. 32 mg).

Granules for tablet cores were made according to the following composition (parts by weight);

| | |
|---|---|
| S-omeprazole Mg-salt | 300 |
| Hydroxypropyl methylcellulose 50 cps | 80 |
| ethanol 95% (w/v) | 356 |
| Polyvinyl pyrrolidone K-90 | 40 |

The powders were mixed in a mixer after which the ethanol was added in an even stream. The mass was dried in a drying oven at 50° C.

After milling in an oscillating mill through a 1.0 mm screen the obtained granules were mixed with tablet lubricant, according to the following composition (parts by weight);

| | |
|---|---|
| Granules for tablet core | 380 |
| Sodium stearyl fumarate (Pruv ®) | 4 |

The mixing was performed in a Kenwood mixer whereafter the mixture was compressed to tablets (7 mm in diameter) having an average weight of 175 mg, on a single punch tableting machine (Diaf).

The prepared tablets can be further processed according to Example 3 or 4, i.e. apply an enteric coating on the tablet.

Example 3

Enteric coated extended release matrix tablets comprising S-omeprazole Mg-salt (approx. 32 mg).

Tablets from example 2 were coated first with a separating layer in a fluidized bed coating apparatus with a coating suspension of the following composition;

| | |
|---|---|
| EtOH 99.5% (w/v) | 85 parts by weight |
| Water purified | 85 parts by weight |
| Hydroxypropyl methylcellulose 6 cps | 10 parts by weight |
| Talc, micronized | 2 parts by weight |
| Sum: | 182 parts. |

200 grams of tablets were processed and the coating was continued until average tablet weight was 181 mg.

The tablets coated with a separating layer were coated with an enteric coating layer in the same equipment as for the preceding coating step. The coating solution used had the following composition;

| | |
|---|---|
| Hydroxypropyl methylcellulose phtalate (HP-55 ®) | 19 parts by weight |
| Cetanol | 1 parts by weight |
| Acetone | 182 parts by weight |
| Ethanol (95% w/v) | 78 parts by weight |
| Sum: | 280 parts |

100 grams of the separating layer coated tablets were processed and the coating was continued until average tablet weight was 194 mg.

The tablets were exposed for 0.1 M HCl for 2 hours. The acid resistance was determined to 98%.

Example 4

Enteric coated extended release matrix tablets comprising S-omeprazole Mg-salt (approx. 32 mg).

The tablets obtained from Example 2 were directly coated with an enteric coating layer in a fluidized bed coating apparatus. The coating solution used had the following composition;

| | |
|---|---|
| Hydroxypropyl methylcellulose phtalate (HP-55 ®) | 19 parts by weight |
| Cetanol | 1 parts by weight |
| Acetone | 182 parts by weight |
| Ethanol (95% w/v) | 78 parts by weight |
| Sum: | 280 parts |

100 grams of the tablets were processed and the coating was continued until average tablet weight was 187 mg.

The tablets were exposed for 0.1 M HCl for 2 hours. The acid resistance was determined to 99%.

Example 5

Extended release matrix tablets comprising S-omeprazole Mg-salt (approx. 45 mg).

Granules for tablet cores were made according to the following composition (parts by weight);

| | |
|---|---|
| S-omeprazole Mg-salt | 45 |
| Polyethylene oxide (m wt approx. 4000 000), Polyox ® WSR 301 | 145 |
| Sodium aluminium silicate | 50 |
| Propyl gallate | 0.1 |
| Ethanol 99.5% (w/v) | 140 |

The powders were mixed and moistened with the ethanol in a mixer after which the mass was dried in a drying oven at 50° C.

After milling in an oscillating mill through a 1.0 mm screen the obtained granules were mixed with tablet lubricant, according to the following composition (parts by weight);

| | |
|---|---|
| Granules for tablet core | 232 |
| Sodium stearyl fumarate (Pruv ®) | 1 |

The ingredients were mixed whereafter the mixture was compressed to tablets (10 mm in diameter) having an average weight of 241 mg, on a single punch tableting machine (Diaf).

Dissolution rate was tested as described in example 1.

The release rate obtained (n=2) is shown in table below;

| Time (Hours) | Released (% of dose) |
|---|---|
| 2 | 16–16 |
| 4 | 29–29 |
| 6 | 41–42 |
| 8 | 53–54 |
| 10 | 65–66 |
| 12 | 76–78 |
| 14 | 88–88 |

-continued

| Time (Hours) | Released (% of dose) |
|---|---|
| 16 | 95–96 |
| 18 | 100–100 |
| 20 | 109–109* |

*) Remark: the complete dose has been released.

Example 6

Extended release matrix tablets comprising S-omeprazole Mg-salt (approx. 45 mg).

Granules for tablet cores were made according to the following composition (parts by weight);

| | |
|---|---|
| S-omeprazole Mg-salt | 45 |
| Polyethylene oxide (m wt approx. 4000 000), Polyox ® WSR 301 | 72.5 |
| Polyethylene oxide (m wt approx. 100 000), Polyox ® WSR N10 | 72.5 |
| Sodium aluminium silicate | 50 |
| Propyl gallate | 0.1 |
| Ethanol 99.5% (w/v) | 140 |

The powders were mixed and moistened with the ethanol in a mixer after which the mass was dried in a drying oven at 50° C.

After milling in an oscillating mill through a 1.0 mm screen the obtained granules were mixed with tablet lubricant, according to the following composition (parts by weight);

| | |
|---|---|
| Granules for tablet core | 234 |
| Sodium stearyl fumarate (Pruv ®) | 1 |

The ingredients were mixed whereafter the mixture was compressed to tablets (10 mm in diameter) having an average weight of 241 mg, on a single punch tableting machine (Diaf).

Dissolution rate was tested as described in Example 1 above.

The release rate obtained (n=2) is shown in table below;

| Time (Hours) | Released (% of dose) |
|---|---|
| 2 | 14–14 |
| 4 | 29–29 |
| 6 | 44–47 |
| 8 | 60–65 |
| 10 | 73–78 |
| 12 | 87–89 |
| 14 | 99–101 |
| 16 | 101–102* |
| 18 | 101–105* |

*) Remark: the complete dose has been released

Example 7

Extended release matrix tablets comprising S-omeprazole Mg-salt (approx. 45 mg).

Granules for tablet cores were made according to the following composition (parts by weight);

| | |
|---|---:|
| S-omeprazole Mg-salt | 45 |
| Polyethylene oxide (m wt approx. 100 000), Polyox ® WSR N10 | 145 |
| Sodium aluminium silicate | 50 |
| Propyl gallate | 0.1 |
| Ethanol 99.5% (w/v) | 140 |

The powder were mixed and moistened with the ethanol in a mixer after which the mass was dried in a drying oven at 50° C.

After milling in an oscillating mill through a 1.0 mm screen the obtained granules were mixed with tablet lubricant, according to the following recipe (parts by weight);

| | |
|---|---:|
| Granules for tablet core | 229 |
| Sodium stearyl fumarate (Pruv ®) | 1 |

The ingredients were mixed whereafter the mixture was compressed to tablets (10 mm in diameter) having an average weight of 241 mg, on a single punch tableting machine (Diaf).

Dissolution rate was tested as described in example 1.
The release rate obtained (n=2) is shown in table below;

| Time (Hours) | Released (% of dose) |
|---|---|
| 2 | 67–68 |
| 4 | 107–110*) |
| 6 | 107–111*) |

*) Remark: The complete dose has been released.

Example 8

Extended release matrix tablets comprising omeprazole Mg-salt (approx. 45 mg).

Granules for tablet cores were made according to the following composition (parts by weight);

| | |
|---|---:|
| Omeprazole Mg-salt | 80 |
| Hydroxypropyl methylcellulose 50 cps | 300 |
| Polyvinyl pyrrolidone K-90 | 40 |
| Ethanol 99.5% (w/v) | 400 |

The polyvinyl pyrrolidone (PVP) was dissolved in the alcohol. The other two ingredients were mixed and then moistened with the PVP-solution in a mixer. Thereafter the obtained mass was dried in a drying oven at 50° C.

After milling in an oscillating mill through a 1.0 mm screen the obtained granules were mixed with tablet lubricant, according to the following composition (parts by weight);

| | |
|---|---:|
| Granules for tablet core | 412 |
| Sodium stearyl fumarate (Pruv ®) | 4 |

The ingredients were mixed whereafter the mixture was compressed to tablets (9 mm in diameter) having an average weight of 265 mg, on a single punch tableting machine (Diaf).

Example 9

Extended release matrix tablets comprising S-omeprazole Mg-salt (approx. 45 mg).

Granules for tablet cores were made according to the following composition (parts by weight);

| | |
|---|---:|
| S-omeprazole Mg-salt | 74 |
| Hydroxypropyl methylcellulose 50 cps | 210 |
| Hydroxypropyl methylcellulose 10000 cps | 90 |
| Polyvinyl pyrrolidone K-90 | 40 |
| Ethanol 99.5% (w/v) | 400 |

The polyvinyl pyrrolidone (PVP) was dissolved in the alcohol. The other ingredients were mixed and then moistened with the PVP-solution in a mixer. Thereafter the obtained mass was dried in a drying oven at 50° C.

After milling in an oscillating mill through a 1.0 mm screen the obtained granules were mixed with tablet lubricant, according to the following composition (parts by weight);

| | |
|---|---:|
| Granules for tablet core | 378 |
| Sodium stearyl fumarate (Pruv ®) | 4 |

The mixing was performed in a mixer, and the mixture was compressed to tablets (9 mm in diameter) having an average weight of 261 mg, on a single punch tableting machine (Diaf).

Dissolution rate was tested in phosphate buffer pH 6.8 as described in example 1.

The release rate obtained (n=6) is shown in table below;

| Time (Hours) | Average (min–max) Released (% of nominal dose) |
|---|---|
| 1 | 8 (8–8) |
| 2 | 16 (16–17) |
| 3 | 26 (25–27) |
| 4 | 35 (34–36) |
| 6 | 54 (52–56) |
| 8 | 72 (70–75) |
| 10 | 86 (83–91) |
| 12 | 92 (90–99) |

Example 10

Extended release matrix tablets comprising S-omeprazole Mg-salt (approx. 55 mg).

Granules for tablet cores were made according to the following composition (parts by weight);

| | |
|---|---:|
| S-omeprazole Mg-salt | 40 |
| Polyvinyl alcohol m wt 22000, degree of hydrolysis 97.5–99.5% | 160 |
| Polyvinyl pyrrolidone K-90 | 14 |
| Ethanol 99.5% (w/v) | 49 |

The polyvinyl pyrrolidone (PVP) was dissolved in the alcohol. The other two ingredients were mixed and then moistened with the PVP-solution in a mixer. Thereafter the obtained mass was dried in a drying oven at 50° C.

After milling in an oscillating mill through a 1.0 mm screen the obtained granules were mixed with tablet lubricant, according to the following composition (parts by weight);

| | |
|---|---|
| Granules for tablet core | 215 |
| Sodium stearyl fumarate (Pruv ®) | 2 |

The ingredients were mixed whereafter the mixture was compressed to tablets (9 mm in diameter) having an average weight of 310 mg, on a single punch tableting machine (Diaf).

Dissolution rate was tested in phosphate buffer pH 6.8 as described in example 1.

The release rate obtained (n=2) is shown in table below;

| Time (Hours) | Released Average (min–max) % (of in tablets found dose) |
|---|---|
| 1 | 5 (5–5) |
| 2 | 15 (15–15) |
| 4 | 24 (23–24) |
| 6 | 31 (30–32) |
| 8 | 38 (37–39) |
| 10 | 44 (43–45) |
| 12 | 50 (49–50) |
| 14 | 55 (55–56) |

What is claimed is:

1. An extended release pharmaceutical dosage form consisting essentially of an active ingredient which is an $H^+$, $K^+$-ATPase inhibitor embedded in a hydrophilic or hydrophobic matrix for the extended release of the active ingredient, optional pharmaceutically acceptable excipients, a water soluble separating layer and an enteric coating layer, and the $H^+$, $K^+$-ATPase inhibitor is a compound of formula I

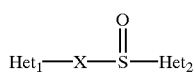

wherein

Het₁ is

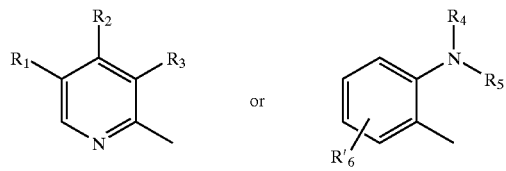

Het₂ is

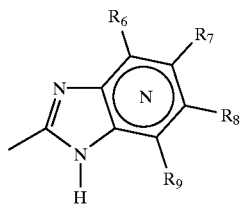 or 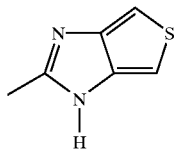

X=

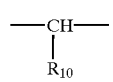 or 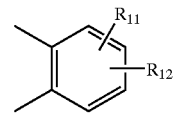

wherein
N in the berzimidazole moiety means that one of the ring carbon atoms substituted by $R_6$–$R_9$ optionally may be exchanged for a nitrogen atom without any substituents;
$R_1$, $R_2$ and $R_3$ are the same or different and selected from the group consisting of hydrogen, alkyl, alkoxy, fluorine-substituted alkoxy, alkylthio, alkoxyalkoxy, dialkylamino, piperidino, morpholino, halogen, phenyl and phenylalkoxy;
$R_4$ and $R_5$ are the same or different and selected from the group consisting of hydrogen, alkyl and arylalkyl;
$R_6'$ is selected from the group consisting of hydrogen, halogen, trifluoromethyl, alkyl and alkoxy; $R_6$–$R_9$ are the same or different and selected from the group consisting of hydrogen, alkyl, alkoxy, halogen, haloalkoxy, alkylcarbonyl, alkoxycarbonyl, oxazolinyl, trifluoroalkyl, or adjacent groups $R_6$–$R_9$ form ring structures which may be further substituted;
$R_{10}$ is hydrogen or forms an alkylene chain together with $R_3$; and $R_{11}$ and $R_{12}$ are the same or different and selected from the group consisting of hydrogen, halogen and alkyl.

2. The dosage form according to claim 1, wherein the $H^+$, $K^+$-ATPase inhibitor is a compound selected from the group consisting of omeprazole, an alkaline salt of omeprazole, the (−)-enantiomer of omeprazole and an alkaline salt of the (−)-enantiomer of omeprazole.

3. The dosage form according to claim 2, wherein the alkaline salt is a magnesium salt.

4. The dosage form according to claim 1, wherein the $H^+$, $K^+$-ATPase inhibitor is a compound selected from the group consisting of lansoprazole, an alkaline salt of lansoprazole, a single enantiomer of lansoprazole, and an alkaline salt of the single enantiomer.

5. The dosage form according to claim 1, wherein the pharmaceutically acceptable excipient is selected form the group consisting of binder, alkaline additives, surfactants, lubricants, fillers, glidants, antioxidants and mixtures thereof.

6. The dosage form according to claim 1, wherein a seed or sphere is layered with the $H^+$, $K^+$-ATPase inhibitor and optional pharmaceutically acceptable excipients.

7. The dosage form according to claim 1, wherein the pH of the micro-environment around the $H^+$, $K^+$-ATPase inhibitor is not less than a pH of 7.

8. The dosage form according to claim 1, wherein the hydrophilic matrix comprises a hydrophilic polymer selected from the group consisting of hydroxypropyl methylcellulose, hydroxypropyl cellulose, ethylhydroxy ethylcellulose, hydroxyethyl cellulose, carboxymethyl cellulose, sodium carboxymethyl cellulose, methyl cellulose, polyethylene oxides, polyvinylpyrrolidone, polyvinyl alcohols, tragacanth, xanthan, and mixtures thereof.

9. The dosage form according to claim 8, wherein the hydrophilic matrix further comprises a filler.

10. The dosage form according to claim 8, wherein the amount of the hydrophilic polymer in the matrix is 15–80% w/w.

11. The dosage form according to claim 9, wherein the filler is selected from the group consisting of sodium aluminum silicate, mannitol and calcium phosphate.

12. The dosage form according to claim 9, wherein the filler is sodium aluminum silicate or calcium phosphate.

13. The dosage form according to claim 12, wherein the amount of the hydrophilic polymer in the matrix is 15–80% w/w and the amount of the filler is 10–60%w/w.

14. The dosage form according to claim 1, wherein the hydrophobic matrix comprises a component selected from the group consisting of a hydrophobic polymer, a hydrophobizing agent and mixtures thereof.

15. The dosage form according to claim 14, wherein the hydrophobic polymer is selected from the group consisting of polyvinyl chloride, ethyl cellulose, polyvinyl acetate, acrylic acid copolymers and mixtures thereof.

16. The dosage form according to claim 14, wherein the hydrophobic matrix further comprises a component selected from the group consisting of sodium aluminum silicate, calcium phosphate, aerosil, titanium dioxide, and magnesium carbonates.

17. The dosage form according to claim 14, wherein the hydrophobizing agent is selected from the group of consisting of cetanol, cetostearyl alcohol, cetyl palmitate, waxes, paraffin, magnesium stearate, sodium stearyl fumarate, medium- and long-chain glycerol esters and mixtures thereof.

18. The dosage form according to claim 1, wherein the $H^+$, $K^+$-ATPase inhibitor is an alkaline salt, a single enantiomer or an alkaline salt of the single enantiomer of the compound of formula I.

19. The dosage form according to claim 1, wherein the $H^+$, $K^+$-ATPase inhibitor is a compound selected from the group consisting of pantoprazole, an alkaline salt of pantoprazole, a single enantiomer of pantoprazole, and an alkaline salt of the single enantiomer.

20. The dosage form according to claim 1, wherein units of the dosage form are in compliance with the requirements regarding gastric acid resistance for enteric coated articles as defined in the United States Pharmacopcia.

21. The dosage form according to claim 20, wherein a dosage unit is in the form of an enteric coated tablet.

22. The dosage form according to claim 20, wherein dosage units are in the form of enteric coated pellets.

23. A capsule comprising the enteric coated pellets according to claim 22.

24. A multiple unit tablet comprising the enteric coated pellets according to claim 22.

25. A process for the manufacture of an extended release dosage form consisting essentially of an active ingredient which is an $H^+$, $K^+$-ATPase inhibitor, optionally pharmaceutically acceptable excipients and a hydrophilic or hydrophobic matrix for the extended release of the active ingredient, wherein the process comprises the following steps:
   a) mixing the $H^+$, $K^+$-ATPase inhibitor, optional pharmaceutically acceptable excipients and the hydrophilic or tie hydrophobic matrix to obtain a core material, and
   b) applying an enteric coating layer onto the core material wherein a water soluble separating layer is applied onto the core material prior to the application of the enteric coating.

26. The dosage form according to any one of claims 1–4, 5–9, 14–16, 11, 17–22 or 10, 12, 13, wherein the extended release is maintained for a minimum of 2 hours and a maximum of 12 hours.

27. A method for improving inhibition of gastric acid secretion comprising administering to a patient in need thereof the dosage form as claimed in any one of claims 1–4, 5–9, 14–16, 11, 17–22 or 10, 12, 13.

28. A method for improving the treatment of gastrointestinal disorders associated with excess acid secretion comprising administering to a patient in need thereof the dosage form as claimed in any one of claims 1–4, 5–9, 14–16, 11, 17–22 or 10, 12, 13.

29. The dosage form according to claim 2, wherein the $H^+$, $K^+$-ATPase inhibitor is S-omeprazole magnesium salt.

30. The dosage form according to claim 1, wherein the water soluble separating layer contains hydroxypropyl methylcellulose.

31. The process according to claim 25, wherein the water soluble separating layer contains hydroxypropyl methylcellulose.

* * * * *

UNITED STATES PATENT AND TRADEMARK OFFICE
CERTIFICATE OF CORRECTION

PATENT NO. : 6,605,303 B1
DATED : August 12, 2003
INVENTOR(S) : Karehill et al.

It is certified that error appears in the above-identified patent and that said Letters Patent is hereby corrected as shown below:

<u>Title page,</u>
Item [56], U.S. PATENT DOCUMENTS, add the following documents:

| Document No. | Date | Name | Class | Sub-Class |
|---|---|---|---|---|
| 3,065,143 | 11/1962 | Christenson et al. | 167 | 82 |
| 4,786,505 | 11/1988 | Lovgren et al. | 424 | 468 |
| 4,853,230 | 08/1989 | Lovgren et al. | 424 | 466 |
| 5,178,867 | 01/1993 | Guittard et al. | 424 | 473 |
| 5,273,758 | 12/1993 | Royce | 424 | 465 |
| 5,330,982 | 07/1994 | Tyers | 514 | 214 |
| 5,753,265 | 05/1998 | Bergstrand et al. | 424 | 474 |
| 5,817,338 | 10/1998 | Bergstrand et al. | 424 | 468 |
| 5,945,124 | 08/1999 | Sachs et al. | 424 | 472 |
| 08/945,425 | 21.10.1997 | Cederberg et al. | | |
| 09/555,720 | 15.01.1999 | Lundberg et al. | | |

FOREIGN PATENT DOCUMENTS, add the following documents:

| Document No. | Date | Country |
|---|---|---|
| 0005129 | 10/1979 | EP |
| 0124495 | 11/1984 | EP |
| 0166287 | 01/1986 | EP |
| 0174726 | 03/1986 | EP |
| 0249587 | 12/1987 | EP |
| 2163747 | 03/1986 | UK |
| 9427988 | 12/1994 | WO |
| 9501977 | 01/1995 | WO |
| 9501783 | 01/1995 | WO |
| 9601623 | 01/1996 | WO |
| 9601624 | 01/1996 | WO |
| 9702020 | 01/1997 | WO |
| 9702021 | 01/1997 | WO |
| 9747285 | 12/1997 | WO |
| 9748380 | 12/1997 | WO |

OTHER PUBLICATIONS, add:

| |
|---|
| Intl. J. Pharmaceutics, Sangalli et al., 1993, 151-156. |
| J. Pharmaceutical Sci., Kim, 1995, 303-306. |
| Intl. J. Pharmaceutics, Romero et al., 1991, 239-248. |
| J. Controlled Release, Franz et al., 1987, 159-172. |
| Scand. J. Gastroenterol., Lind et al., 1986, 137-138 |
| Scand. J. Gastroenterol., Lind et al. 1988, 23, 1259-1266 |
| Remington's Pharmaceutical Sciences, John E. Hoover, 1975, p. 702 |
| Gut, Lind et al., 1983, 270-276 |
| "Perspektiven der Therapie mit Protonenpumpenblockern (PP-Blocker)", Blum, A.L., <u>Gastroenterol</u> (Suppl.1) 1995; 33:32-40. |
| Pharmaceutics: The Science of Dosage Form Design , Aulton, M.E. (Churchill Livingstone Ed.), (1988) pp. 316-321. |

UNITED STATES PATENT AND TRADEMARK OFFICE
CERTIFICATE OF CORRECTION

PATENT NO.      : 6,605,303 B1
DATED           : August 12, 2003
INVENTOR(S)     : Karehill et al.

It is certified that error appears in the above-identified patent and that said Letters Patent is hereby corrected as shown below:

<u>Column 4,</u>
Line 16, insert -- or -- before "hydrophilic --.

<u>Column 9,</u>
Line 10, delete "hydrophobic may be used polymers" and substitute therefor -- hydrophobic polymers may be used --.
Line 51, add -- or -- before "centrifugal --.

<u>Column 17,</u>
Line 58, delete "Hetis" and substitute therefor -- $Het_1$ is --.

<u>Column 18,</u>
Line 21, delete "berzimidazole" and substitute therefor -- benzimidazole --.
Line 57, delete "binder" and substitute therefor -- binders --.

<u>Column 20,</u>
Line 2, delete "Pharmacopcia" and substitute therefor -- Pharmacopeia --.
Line 20, delete "tie" and substitute therefor -- the --.

Signed and Sealed this

Sixth Day of January, 2004

JAMES E. ROGAN
*Director of the United States Patent and Trademark Office*